United States Patent [19]

Myerson

[11] Patent Number: 4,550,198
[45] Date of Patent: Oct. 29, 1985

[54] PURIFICATION OF TEREPHTHALIC ACID BY SUPERCRITICAL FLUID EXTRACTION

[75] Inventor: Allan S. Myerson, Marietta, Ga.

[73] Assignee: Georgia Tech Research Institute, Atlanta, Ga.

[21] Appl. No.: 439,329

[22] Filed: Nov. 4, 1982

[51] Int. Cl.$^4$ ............................................. C07C 51/43
[52] U.S. Cl. ...................................... 560/486; 560/485
[58] Field of Search ........................................... 562/486

[56] References Cited

U.S. PATENT DOCUMENTS

| | | | |
|---|---|---|---|
| 2,923,736 | 2/1960 | MacLean | 562/486 |
| 3,624,145 | 2/1969 | Brinn | 562/486 |
| 3,859,344 | 1/1975 | Shigeyasu et al. | 562/487 X |
| 3,862,218 | 1/1975 | Stautzenberger | 562/486 |
| 3,969,196 | 7/1976 | Zosel | 203/49 |
| 4,212,895 | 7/1980 | Laws et al. | 426/600 |
| 4,218,491 | 8/1980 | Laws et al. | 426/600 |
| 4,298,626 | 11/1981 | Laws et al. | 426/600 |

*Primary Examiner*—Natalie Trousof
*Assistant Examiner*—Vera C. Clarke
*Attorney, Agent, or Firm*—Newton, Hopkins & Ormsby

[57] ABSTRACT

A process for the purification of terephthalic acid comprising (1) contacting an impure terephthalic acid with an amount of supercritical fluid, at a temperature and pressure, and for a period of time, sufficient to dissolve the terephthalic acid and its impurities in said supercritical fluid and (2) allowing said solution of terephthalic acid and impurities in supercritical fluid to expand into a reaction chamber, whereby the supercritical fluid becomes gaseous and the terephthalic acid, freed of impurities, precipitates out as a solid.

12 Claims, 1 Drawing Figure

PURIFICATION OF TEREPHTHALIC ACID BY SUPERCRITICAL FLUID EXTRACTION

BACKGROUND OF THE INVENTION

1. Field of the Invention

This invention relates to a process for producing highly purified terephthalic acid for use in the production of polyester fibers.

2. Description of the Prior Art

The most commercially important linear polyester, polyethylene terephthalate, is produced in two ways. In the first method, the ester is produced through a two-step ester interchange reaction between dimethyl terephalate and ethylene glycol, the first step consisting of an exchange of two molecules of methanol for two molecules of ethylene glycol, the second step consisting of a transesterification reaction whereby one molecule of ethylene glycol is split off.

Polyethylene terephthalate may also be produced by the direct condensation of terephthalic acid with ethylene glycol, a process which has considerable economic advantages over the method employing dimethyl terphthalate. However, this method requires the use of terephthalic acid essentially free from impurities in order to produce fiber grade polyester terephthalate, the presence of impurities imparting an unacceptable yellow coloration to the fibers as well as lowering the melting point and crystallinity to unacceptable levels.

Terephthalic acid is prepared by the oxidation of p-xylene in the liquid phase with a molecular oxygen-containing gas such as air in a lower carboxylic acid solvent in the presence of a heavy metal-containing catalyst at elevated temperature and pressure. The crude terephthalic acid thus obtained is, however, contaminated with oxidation intermediates, particularly 4-carboxybenzaldehyde which may be present in amounts of 1% or more.

Since terephthalic acid is only sparingly soluble in most solvents and melts only at temperatures above 425° C., a temperature at which decomposition begins, conventional purification methods such as recrystallization and distillation are not available. And while it is known that 4-carboxybenzaldehyde can be easily oxidized to terephthalic acid, as an impurity in the terephthalic acid it exists in the crystal lattice, intimately bound in such a way as to make it impervious to attempts to oxidatively convert it to terephthalic acid.

British Pat. No. 982,629 discloses a method whereby crude terephthalic acid is subjected to a secondary oxidation step in acetic acid at 250° C. In this process the 4-carboxybenzaldehyde contained in the solid terephthalic acid particles is dissolved and can be oxidized. This method is, however, quite uneconomical because at temperatures above 200° C., the acetic acid is both unstable and highly degradative to the equipment employed for the processing, while at temperatures below 200° C., the solubility of terephthalic acid is too low to be practical.

British Pat. No. 1,454,478 discloses a method whereby a secondary oxidation of a slurry to terephthalic acid in acetic acid at 190°-195° C. is attempted. However, this method requires extremely long oxidation times and achieves only a limited purification, making it useful at best only when there are very low levels of 4-carboxybenzaldehyde to start.

Similarly, U.S. Pat. No. 3,859,344 discloses a secondary oxidation of a crude terephthalic acid which involves residence time in several different crystallizers with only a minimal purifiication effect.

U.S. Pat. No. 3,660,478 suggests circulating a slurry of crude terephthalic acid in acetic acid through a crystallizing loop at least ten times. In this process 1 to 10% of the dissolved terephthalic acid is recrystallized with each pass, a process which is highly inefficient.

U.S. Pat. No. 3,624,145 discloses a method whereby a liquid-liquid extraction process is employed. An aqueous solution of crude terephthalic acid is contacted with a water-immiscible liquid organic extractant inert to terephthalic acid but capable of dissolving out the impurities followed by separation of the two phases. The process requires repeating the procedure many time until the proper degree of purification is obtained and also requires that large volumes of water be employed, thereby creating severe efficiency and handling problems.

Therefore a need has continued to exist for a process for purifying terephthalic acid to remove various impurities, including oxidative intermediates, particularly 4-carboxybenzaldehyde, whereby these oxidative intermediates can be freed up so as to permit their subsequent oxidation to terephthalic acid.

BRIEF DESCRIPTION OF THE DRAWINGS

The present invention will be better understood by reference to the drawing and the following description which refers to the accompanying in which:

a schematic showing the TPR purification process is depicted.

SUMMARY OF THE INVENTION

Figure 1:
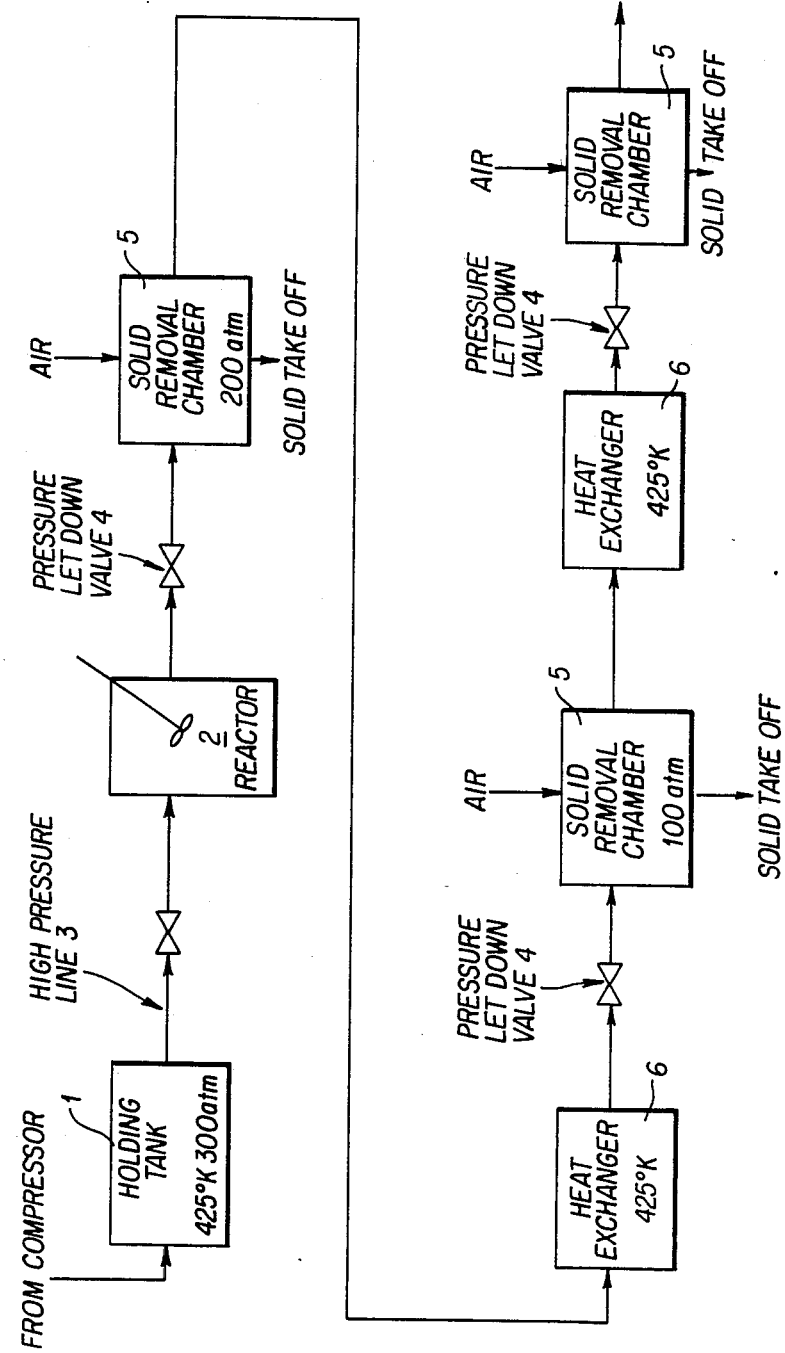

It is, therefore, an object of this invention to prepare terephthalic acid in highly purified form.

It is a further object of this invention to prepare terephthalic acid in highly purified form wherein impurities which are oxidative intermediates are further oxidized to terephthalic acid.

It is yet a further object of this invention to produce terephthalic acid in highly purified form suitable for direct esterification to polyethylene terephthalate by reaction with ethylene glycol.

These and other objects of the invention, as will hereinafter become more readily apparent have been accomplished by a process for the purification of terephthalic acid comprising contacting the crude terephthalic acid with an amount of supercritical fluid, at a pressure and temperature and for a period of time, sufficient to totally dissolve the terephthalic acid whereby the terephthalic acid and its impurities are completely dissolved in said supercritical fluid and then allowing the solution of terephthalic acid in supercritical fluid to expand into a reaction chamber whereby the supercritical fluid becomes a gas and the terephthalic acid, freed of impurities, precipitates out as a solid. Impurities which are oxidative intermediates, such as 4-carboxybenzaldehyde are oxidized to terephthalic acid by the introduction of molecular oxygen.

DESCRIPTION OF THE PREFERRED EMBODIMENT

By crude terephthalic acid is meant the terephthalic acid product resulting from the oxidation of a p-alkylbenzene. These methods are well-known in the art and are not a part of this invention. One such method involves oxidizing a p-alkylbenzene such as p-xylene in the liquid phase with a molecular-oxygen containing gas, such as air, in a lower aliphatic carboxylic acid solvent, in the presence of a heavy metal-containing oxidation catalyst at elevated temperature and elevated pressure. The crude terephthalic acid, produced by conventional processes, may have been subjected to purification steps well-known in the art, such as leaching with warm acetic acid to remove catalyst residues and p-toluic acid prior or subsequent to the practice of this invention.

By "contacting" is meant any and all of the conventional and well-known methods for admixing materials. Representative, but not limiting, examples include mechanical agitation, air agitation, tumbling, shaking, and magnetic stirring.

By supercritical fluid is meant a gas subjected to a pressure sufficient to impart to said gas a density equal to its liquid density, said pressure exerted at a temperature above the critical temperature of said gas. Critical temperature being is as that temperature above which pressure liquification cannot occur. These supercritical fluids and their critical temperatures and pressures are well known in the art. Nonlimiting examples of gases from which supercritical fluid can be derived are carbon dioxide, ammonia, water, methane, ethane, n-propane, n-butane, n-pentane, n-hexane, n-heptane, 2,3-dimethylbutane, benzene, diethyl ether, toluene, dichlorodifluoromethane, trichlorofluoromethane, dichlorotetrafluoroethane, and chlorotrifluoromethane. Carbon dioxide is the preferred gas for practicing this invention. These compounds have critical temperatures in the range of 191° K. to 647° K. On principle, compounds having critical temperatures in the range of 273° K. to 573° K., are preferred from an energy use concept.

While the solubility of terephthalic acid varies according to the particular supercritical fluid involved, satisfactory solubility in each of the disclosed gases can be effected by suitably varying the temperature and pressure during the dissolution step of the process. Temperature ranges of 191° K. to 1000° K. and pressure ranges of 25 atmospheres to 1000 atmospheres are within the contemplation of this invention; however, a temperature range of 273° K. to 573° K. and pressure range of 27 to 75 atmospheres is preferred.

The period of time required to effect dissolution is a function of the particular gas being used as well as the temperature and pressure. Typical time requirements are from a few seconds to several hours or more. In general, economic factors make it preferable to effect dissolution in as short at time as possible.

Solution concentrations can vary from extremely dilute solutions, on the order to 5% by weight or less, to extremely concentrated solutions of 85% by weight or higher. A preferred concentration range is 15 to 45% by weight, with 20 to 30% by weight being most preferred.

Crude terephthalic acid obtained, for example, by the oxidation of p-xylene with molecular oxygen is contacted with a supercritical fluid at such temperature, pressure and time as required to completely dissolve the terephthalic acid and its impurities. The solution of terephthalic acid and its impurities in the supercritical fluid are then allowed to expand into a reaction chamber containing molecular oxygen whereby the supercritical fluid becomes gaseous and the terephthalic acid precipitates out as a crystalline solid. The gaseous residue of the supercritical fluid, for example carbon dioxide, may be recirculated through a compressor where it is compressed, at a temperature slightly in excess of its critical temperature, to a supercritical fluid state, to be recycled back into the process. The oxidative intermediates, before chemically bound in the crystal lattice structure of the terephthalic acid, upon exposure to the molecular oxygen in the reaction chamber, are converted to terephthalic acid. The resulting product is an essentially pure terephthalic acid which is suitable for the production of fiber grade polyethylene terphthalate by direct esterification with ethylene glycol.

4-carboxybenzaldehyde, present in the starting material at levels of 1-2% by weight or higher may be reduced to levels of 500 ppm or lower, with levels as low as 5 ppm attainable through careful selection of supercritical fluid and temperaturetime parameters.

Having now generally described this invention, the same will be better understood by reference to certain specific examples, which are included herein for purposes of illustration only and are not intended to be limiting of the invention or any embodiment thereof, unless specified.

EXAMPLE 1—BATCH PROCESS

Supercritical carbon dioxide at 425° K. and 300 atm is stored in holding tank 1. The carbon dioxide is periodically introduced into the magnetically stirred reactor 2 (which contains the terephthalic acid to be purified) through the high pressure line 3. After remaining in the reactor for a time period sufficient to dissolve a large portion of the terephthalic acid in the reactor, the supercritical carbon dioxide with dissolved terephthalic acid in it is passed through a series of pressure let down valves 4. Heat exchangers 6 are provided to keep the temperature of the batch from dropping. Air (as a source of oxygen) is added in each precipitation stage 5 to provide the oxidant from precipitated 4carboxybenzaldehyde to react to form terephthalic acid. Terephthalic acid precipitated at the end of each pressure reduction step is collected at the end of each batch run. Carbon dioxide is then recycled back to a compressor. A diagram of the process with conditions appears as FIG. 1.

EXAMPLE 2—CONTINUOUS PROCESS

Supercritical carbon dioxide at 425° K. and 300 atm is stored in a holding tank and is continuously added to column 2 which is packed with terephthalic acid. Carbon dioxide with terephthalic acid dissolved in it leaves the column at the bottom where it passes through a series of pressure reducing valves and heat exchangers as in Example 1. The process is continuous, but must be shut down periodically to replenish the terephthalic acid in the column.

EXAMPLE 3

Same as 1 using water as the supercritical fluid 600° K. 200 atm).

EXAMPLE 4

Same as 2 using water as the supercritical fluid (600° C. 200 atm).

The invention now being fully described, it will be apparent to one with ordinary skill in the art that many changes and modifications can be made thereto without departing from the spirit or scope of the invention as set forth herein.

What is claimed as new and desired to be secured by Letters Patent of the United States is:

1. The process of purifying terephthalic acid which comprises the steps of:
   (a) dissolving impure terephthalic acid while at a temperature in the range of 191° K. to 1000° K. and a pressure within the range of 25 atm to 1000 atm in a fluid which is supercritical at the temperature and pressure of the dissolution to form a solution of impure terephthalic acid in the supercritical fluid;
   (b) extending said solution to a reduced pressure to precipitate purified terephthalic acid as a solid; and
   (c) recovering the precipitated terephthalic acid.

2. The process as defined in claim 1 wherein the pressure of step (a) is about 300 atmospheres and the critical temperature of the fluid is in the range of 191° K. to 647° K.

3. The process as defined in claim 1 wherein step (b) is effected in discrete stages and including the step of heating terephthalic acid-depleted solution between stages so as to maintain the temperature substantially that of step (a).

4. The process of claim 1 wherein the supercritical fluid is selected from the group consisting of carbon dioxide, ammonia, water, methane, ethane, n-propane, n-butane, n-pentane, n-hexane, n-heptane, 2,3-dimethylbutane, benzene, diethyl ether, toluene, dichlorodifluoromethane, trichlorofluoromethane, dichlorotetrafluoroethane, and chlorotrifluoromethane.

5. The process of claim 4 wherein the supercritical fluid is supercritical carbon dioxide.

6. The process as defined in claim 3 including the steps of contacting said solution with molecular oxygen in each of said stages to precipitate essentially pure terephthalic acid in each of said stages.

7. The process as defined in any one of claims 1 to 3 wherein step (b) is effected in the presence of molecular oxygen to precipitate essentially pure terephthalic acid.

8. The method of purifying terephthalic acid preparatory to the direct esterfying reaction thereof with ethylene glycol to produce polyethylene terephthalate, which comprises the steps of:
   (a) providing a supply of supercritical fluid having a temperature in the range of about 191°–647° K. and a pressure of not more than about 300 atmospheres so as to be capable of dissolving impure terephthalic acid;
   (b) contacting supercritical fluid from the supply of step (a) with impure terephthalic acid to form a solution of impure terephthalic acid in said supercritical fluid, said solution containing at least about 5% by weight of impure terephthalic acid;
   (c) expanding the solution of step (b) to a reduced pressure into a reaction chamber while contacting it with molecular oxygen to precipitate essentially pure terephthalic acid; and
   (d) recovering the precipitate of step (c).

9. The method as defined in claim 8 wherein the supercritical fluid is selected from the group consisting of carbon dioxide, ammonia, water, methane, ethane, n-propane, n-butane, n-pentane, n-hexane, n-heptane, 2,3-dimethylbutane, benzene, diethyl ether, dichlorodifluoromethane, trichlorofluoromethane, dichlorotetrafluoroethane, and chlorotrifluoromethane.

10. The method as defined in claim 9 wherein the supercritical fluid is carbon dioxide and the supercritical carbon dioxide formed in step (a) is at a temperature of about 425° K. and a pressure of about 300 atm.

11. The method as defined in any one of claims 8–10 wherein step (c) is effected in discrete stages into a series of reaction chambers of successively reduced pressures.

12. The method as defined in claim 10 wherein step (c) is effected in a first reaction chamber at a temperature of 425° K. and a pressure of 200 atmospheres and subsequently in a second reaction chamber at a temperature of 425° K. and a pressure of 100 atmospheres.

* * * * *